(12) United States Patent
Gershenson

(10) Patent No.: US 6,982,790 B1
(45) Date of Patent: Jan. 3, 2006

(54) COHERENT IMAGING IN TURBID MEDIA

(75) Inventor: Meir Gershenson, Panama City, FL (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/014,011

(22) Filed: Jan. 27, 1998

(51) Int. Cl.
G01B 9/02 (2006.01)

(52) U.S. Cl. ...................................... 356/349
(58) Field of Classification Search ............ 356/345, 356/357, 349; 250/227.19, 227.27
See application file for complete search history.

(56) References Cited

U.S. PATENT DOCUMENTS 5,459,570 A * 10/1995 Swanson et al. ............ 356/345
5,565,986 A * 10/1996 Knuttel ........................ 356/345

* cited by examiner

*Primary Examiner*—Samuel A. Turner
(74) *Attorney, Agent, or Firm*—Harvey A. Gilbert; Donald G. Peck

(57) ABSTRACT

A system for forming an image of an object in a turbid medium comprises a light source for producing a coherent light beam of a selected frequency that is divided by a beamsplitter into a reference beam directed along a first optical path and a signal beam directed along a second optical path where the object to be imaged is located. The signal beam impinges upon the object and reflects back toward the beamsplitter. The reference beam is modulated to shift its frequency. A mirror reflects the reference beam back toward the beamsplitter for combination with the signal beam to produce an output optical signal. A photodetector receives the output optical signal from the beamsplitter and produces an electrical signal having a frequency related to shifts in frequency between the reference beam and the signal beam and having an amplitude proportional to the image intensity. A heterodyne detector connected to the photodetector produces a beat signal when the first and second optical paths have matching lengths so that the location of the point on the object where the signal beam reflected can be determined. By scanning the signal beam across the object, the system determines locations of a number of points on the object sufficient to form its image.

6 Claims, 1 Drawing Sheet

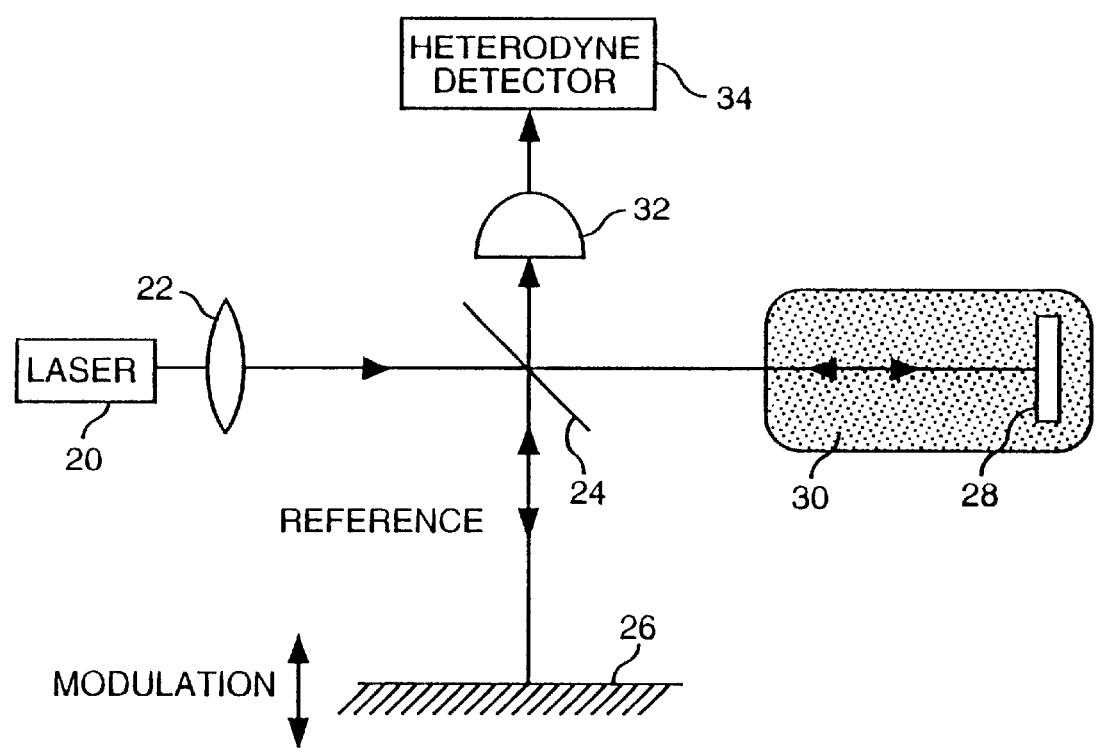

COHERENT IMAGING IN TURBID MEDIA

BACKGROUND OF THE INVENTION

1. Field of the Invention

This invention relates generally to detecting objects imbedded in turbid media such as smoke, fog and water. This invention relates particularly to heterodyning optical signals to enhance a desired signal while averaging out scattered and ambient noise. Still more particularly this invention relates to a using heterodyne detection in a laser-line-scan system for increasing signal-to-noise and resolution in diverse applications such as mine hunting, diving, salvage and medical imaging.

2. Description of the Prior Art

The difficulties detecting objects imbedded in turbid media are well known. In laser-based systems, the primary causes of image degradation are the short range due to high extinction coefficients for turbid media and the large return of backscattered, forward-scattered, and ambient light into the detector washing out the signal. The scattering problem is reduced, but not eliminated by range-gating and line-scan systems.

The scattered light cannot be used to reconstruct high resolution images using conventional imaging techniques. The contrast of the image is further reduced as a result of light scattered by the turbid medium directly into the camera.

SUMMARY OF THE INVENTION

A system according to the present invention for forming an image of an object in a turbid medium, comprises a light source for producing a coherent light beam of a selected frequency to a beamsplitter. The beamsplitter divides the coherent light beam to produce a reference beam directed along a first optical path and a signal beam directed along a second optical path where the object to be imaged is located. The signal beam impinges upon the object and reflects back toward the beamsplitter. A mirror is arranged to reflect the reference beam back toward the beamsplitter for combination with the signal beam to produce an output optical signal. A photodetector receives the output optical signal from the beamsplitter and produces an electrical signal having a frequency related to shifts in frequency between the reference beam and the signal beam and having an amplitude proportional to the image intensity. A heterodyne detector is connected to the photodetector and arranged to produce a beat signal when the first and second optical paths have matching lengths within the coherence length overlap. Unscattered light will from a coherent heterodyne within the reference beam. The method can also be used to determine the location of the point on the object where the signal beam reflected. By scanning the signal beam across the object, the system determines locations of a number of points on the object sufficient to form its image.

The system according to the present invention preferably determines the locations of points on the object by modulating the optical path of the reference beam and detecting when the reference beam and the signal beam have identical optical path lengths. The modulation shifts the frequency of the reference beam and may be accomplished by moving the mirror relative to the beamsplitter.

An appreciation of the objectives of the present invention and a more complete understanding of its structure and method of operation may be had by studying the following description of the preferred embodiment and by referring to the accompanying drawing.

BRIEF DESCRIPTION OF THE DRAWING

The FIGURE illustrates a system for measuring the scattered spectrum of a laser beam after the beam has interacted with an object submerged in a turbid medium.

DESCRIPTION OF THE PREFERRED EMBODIMENT

This disclosure describes an apparatus and a method for making and using a system for coherent imaging in turbid media. Specific details are disclosed to provide a thorough description of the invention. However, it will be apparent that the present invention may be practiced without these specific details. Well-known components of are shown in block diagram form, rather than in detail, to avoid unnecessarily obscuring the invention.

Referring to the FIGURE, a laser 20 provides a coherent optical signal to a lens 22. After passing through the lens 22, the laser light impinges upon a beamsplitter 24. The beamsplitter 24 reflects part of the incident source light to a mirror 26 that is arranged to reflect the incident beam back toward the beamsplitter 24. The light that is reflected from the mirror 26 back to the beamsplitter 24 is a reference beam for the system.

Part of the source light incident upon the beamsplitter 24 is transmitted toward a target 28 that is submerged in a turbid medium 30. Ordinarily, the precise location of the object 28 is unknown. The present invention provides means for determining the location of the object 28. The laser beam is scanned over the region where the target 28 is located. Scanning may be accomplished by any convenient means known in the art, for example, by moving the laser 20 or by using rotating mirrors (not shown) to direct the beam to selected locations in the turbid medium 30.

The turbid medium 30 scatters some of the light as described above. Part of the light transmitted through the beamsplitter 24 reaches the target 28 and reflects from the target 28 back to the beamsplitter 24 without being scattered. The light reflected from the target 28 to the beamsplitter 24 is the signal beam. The beamsplitter 24 reflects the reference beam and the signal beam to a photodetector 32.

The position of the mirror 26 relative to the beamsplitter 24 may be varied to provide a modulation to the reference beam. The modulation changes the path length of the reference beam. The result of the modulation is equivalent to a phase change with the frequency and phase modulation being related by the equation $f=dF/dt$, which is the well-known Doppler effect. The frequency is shifted to heterodyne the reference beam and the signal beam to obtain a low frequency signal that can be used to detect the coherent portion of the signal.

Light generated by an incoherent source usually contains short packet of light that is coherent over a few thousand cycles. Different packets are incoherent in phases so that heterodyning between them will statistically average to give a noisy detection. If the same light is split by the beamsplitter 24 with one part being shifted in frequency and then heterodyned with the other part, modulation will result because individual packets will be heterodyned with themselves. A beat signal is obtained when the optical paths match. The optical path length of the reference beam is known, therefore the optical path length of the signal beam becomes known when the optical paths match. By scanning the signal beam across the object, the system determines the locations of a number points on the object sufficient to form an image thereof.

The position of the mirror 26 is modulated through a range of motion so that the desired match in path length occurs. As the mirror 26 moves away from a position where the optical path lengths of the two beams match, the coherence decreases so that there is no beat signal. The amount of path length difference that supports interference is related to the coherence length. This effect is the basis for the use of coherent tomography in ophthalmology for mapping the shape of a retina.

The photodetector 32 receives the reference beam and the signal beam that has reflected from the object. The photodetector 32 has optical inputs for the signal beam that contains the image information and for the modulated reference beam. The photodetector 32 forms electrical signals that indicate the intensity of the optical beams incident thereon. The electrical output of the photodetector 32 is input to a heterodyne detector 34.

The heterodyne detector 34 receives from the photodetector 32 an AC signal at a frequency related to the frequency shift between the original signal and the reference signal and noise related to the scattered light. The amplitude of the AC signal is proportional to the image intensity. The amplitude of the noise is related to the scattered light.

In general, the present invention may be practiced using either a light source having either high coherence as described above or low coherence as used in ophthalmology. The coherence is usually measured by the coherence length. Light with low coherence used in ophthalmology typically has a coherence length of a few microns. Laser light typically has a coherence length of a few meters. An advantage of low coherency is high sensitivity to distance in matching optical path lengths. For medical applications, depth determination is very important.

For underwater imaging exact matching is difficult to achieve. In underwater imaging, a clear picture is generally more important than depth. Therefore, using a laser light with sufficient coherence length with a predetermined optical path, using fiber optic cable, for example, allows detection within the coherence length overlap. By limiting the depth range using light of an intermediate coherence length, it is possible to increase image clarity by eliminating coherent sources from the volume between the target and the detector.

An exemplary embodiment of the invention is disclosed herein to explain how to make and use the invention. The described embodiments are to be considered in all respects as exemplary and illustrative rather than restrictive. Therefore, the appended claims rather than the foregoing descriptions define the scope of the invention. All modifications to the embodiments described herein that come within the meaning and ranges of equivalence of the claims are embraced within the scope of the invention.

What is claimed is:

1. A system for forming an image of an object in a turbid medium, comprising:

a laser light source for producing a coherent light beam of a selected frequency;

a lens arranged to receive the coherent light beam output from the laser;

a beamsplitter arranged to receive the coherent light beam that has passed through the lens and produce a reference beam directed along a reference optical path and a signal beam that is directed along a signal optical path to impinge upon the object in the turbid medium and reflect back toward the beamsplitter;

means for modulating the reference beam;

a mirror arranged to reflect the reference beam back toward the beamsplitter for combination with the signal beam to produce an output optical signal, the output optical signal having a beat frequency when the signal beam and the modulated reference beam have equal optical path lengths;

a photodetector arranged to received the output optical signal from the beamsplitter; and a heterodyne detector connected to the photodetector and arranged to produce a beat signal when the first and second optical paths have matching lengths.

2. The system of claim 1, further comprising means for modulating the reference optical path and means for detecting when the modulated first optical path and the second optical path have identical lengths.

3. The system of claim 1, further comprising:

means for shifting the frequency of the reference beam;

means for heterodyning the frequency shifted reference beam with the signal beam.

4. A method for forming an image of an object in a turbid medium, comprising the steps of:

producing a coherent laser light beam of a selected frequency;

arranging a beamsplitter to receive the coherent laser light beam and produce a reference beam directed along a reference optical path and a signal beam directed along a signal optical path to impinge upon the object and reflect back toward the beamsplitter;

modulating the reference beam;

arranging a mirror to reflect the reference beam back toward the beamsplitter for combination with the signal beam to produce an output optical signal, the output optical signal having a beat frequency when the signal beam and the modulated reference beam have equal optical path lengths; and producing a beat signal when the reference and second optical paths have matching lengths.

5. The method of claim 4, wherein the step of modulating the first optical path and detecting when the modulated reference optical path and the signal optical path have identical lengths.

6. The method of claim 4, further comprising the steps of:

shifting the frequency of the reference beam;

heterodyning the frequency shifted reference beam with the signal beam; and detecting beat signals that occur when the reference beam and the signal beam have matching optical path lengths.

* * * * *